(12) United States Patent
Boettger et al.

(10) Patent No.: US 11,058,319 B2
(45) Date of Patent: Jul. 13, 2021

(54) METHOD FOR POSITIONING A POSITIONABLE TABLE

(71) Applicant: Siemens Healthcare GmbH, Erlangen (DE)

(72) Inventors: Thomas Boettger, Erlangen (DE); Daniel Lerch, Weilersbach (DE); Carsten Thierfelder, Pinzberg (DE); Lisa Vallines, Majadahonda (DE); Fernando Vega, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 481 days.

(21) Appl. No.: 15/623,515

(22) Filed: Jun. 15, 2017

(65) Prior Publication Data

US 2017/0311842 A1 Nov. 2, 2017

(30) Foreign Application Priority Data

Jun. 29, 2016 (DE) .......................... 102016211720.3

(51) Int. Cl.
*A61B 5/00* (2006.01)
*A61B 5/055* (2006.01)
*A61B 6/04* (2006.01)
*A61B 6/03* (2006.01)

(52) U.S. Cl.
CPC ............ *A61B 5/055* (2013.01); *A61B 6/0407* (2013.01); *A61B 6/0487* (2020.08); *A61B 6/03* (2013.01); *A61B 6/04* (2013.01)

(58) Field of Classification Search
None
See application file for complete search history.

(56) References Cited

U.S. PATENT DOCUMENTS

| | | | | | |
|---|---|---|---|---|---|
| 4,230,129 | A | * | 10/1980 | LeVeen | A61B 6/12 250/369 |
| 4,770,182 | A | * | 9/1988 | Damadian | A61B 5/0555 324/306 |
| 5,349,956 | A | * | 9/1994 | Bonutti | A61B 5/0555 5/601 |
| 5,376,796 | A | * | 12/1994 | Chan | G01B 11/2433 250/363.02 |

(Continued)

FOREIGN PATENT DOCUMENTS

| CN | 101548888 B | 2/2013 |
|---|---|---|
| CN | 103892863 A | 7/2014 |

(Continued)

OTHER PUBLICATIONS

German Office Action dated May 3, 2017.

(Continued)

*Primary Examiner* — Joanne M Hoffman
(74) *Attorney, Agent, or Firm* — Harness, Dickey & Pierce, P.L.C.

(57) ABSTRACT

A method is for positioning a positionable table for a patient inside a medical imaging device. In an embodiment, the method includes a determination of a table position as a function of an organ or body part of the patient for examination; an ascertainment of correction data for correcting the table position; a determination of a corrected table position based on the ascertained correction data; and a positioning of the table at the corrected table position.

21 Claims, 3 Drawing Sheets

(56) References Cited

U.S. PATENT DOCUMENTS

| | | | | |
|---|---|---|---|---|
| 5,808,468 | A * | 9/1998 | Bis | A61B 5/0555 324/318 |
| 5,983,424 | A * | 11/1999 | Naslund | A61B 6/0421 5/601 |
| 6,294,915 | B1 * | 9/2001 | Murphy | A61B 5/0555 324/318 |
| 6,640,364 | B1 * | 11/2003 | Josephson | A61B 5/0555 378/209 |
| 2002/0044059 | A1 * | 4/2002 | Reeder | G08B 21/02 340/573.1 |
| 2002/0193685 | A1 * | 12/2002 | Mate | A61N 5/1049 600/424 |
| 2003/0230723 | A1 * | 12/2003 | Garrard | G01T 1/1648 250/363.1 |
| 2004/0057557 | A1 * | 3/2004 | Nafstadius | A61B 6/04 378/209 |
| 2005/0074085 | A1 * | 4/2005 | Hsieh | G01N 23/046 378/4 |
| 2005/0129180 | A1 * | 6/2005 | Tsujii | A61B 6/488 378/195 |
| 2005/0152492 | A1 * | 7/2005 | Yakubovsky | A61B 6/04 378/20 |
| 2005/0228255 | A1 * | 10/2005 | Saracen | A61B 6/0457 600/407 |
| 2006/0036160 | A1 * | 2/2006 | Altman | A61B 6/0457 600/415 |
| 2007/0135703 | A1 * | 6/2007 | Rietzel | A61B 6/547 600/407 |
| 2007/0225588 | A1 * | 9/2007 | Steckner | G06Q 50/22 600/407 |
| 2008/0031414 | A1 * | 2/2008 | Coppens | A61B 6/0492 378/65 |
| 2008/0211495 | A1 * | 9/2008 | Steckner | G01R 33/34084 324/300 |
| 2009/0003532 | A1 * | 1/2009 | Weber | A61B 6/0457 378/209 |
| 2009/0052760 | A1 * | 2/2009 | Smith | G06T 17/205 382/132 |
| 2009/0285357 | A1 * | 11/2009 | Khamene | A61B 6/5217 378/20 |
| 2009/0306494 | A1 * | 12/2009 | Scarth | A61B 5/0555 600/411 |
| 2011/0293065 | A1 * | 12/2011 | Kargar | A61B 6/0492 378/62 |
| 2012/0108952 | A1 * | 5/2012 | Stern | A61B 6/58 600/415 |
| 2013/0235969 | A1 * | 9/2013 | Winter | G01R 33/4812 378/4 |
| 2013/0239331 | A1 * | 9/2013 | Eaton | A61B 17/2255 5/601 |
| 2013/0345573 | A1 * | 12/2013 | Kargar | A61B 5/021 600/485 |
| 2014/0058213 | A1 * | 2/2014 | Abu-Tarif | A61B 5/0205 600/301 |
| 2014/0128724 | A1 * | 5/2014 | Dahan | A61B 5/0555 600/415 |
| 2014/0210468 | A1 | 7/2014 | Xu | |
| 2015/0164460 | A1 | 6/2015 | Liu | |
| 2015/0253979 | A1 | 9/2015 | Popescu | |
| 2015/0297164 | A1 | 10/2015 | Dankerl et al. | |
| 2016/0045173 | A1 * | 2/2016 | Bailey | A61B 6/032 378/20 |
| 2016/0274782 | A1 * | 9/2016 | Keil | G06F 3/0482 |
| 2018/0249980 | A1 * | 9/2018 | DiNitto | A61B 6/0421 |
| 2018/0280223 | A1 * | 10/2018 | Hiratsuka | A61G 13/101 |
| 2019/0029559 | A1 * | 1/2019 | Nufer | G01R 33/34092 |

FOREIGN PATENT DOCUMENTS

| | | | |
|---|---|---|---|
| CN | 103961133 | A | 8/2014 |
| CN | 104068886 | A | 10/2014 |
| CN | 104887312 | A | 9/2015 |
| CN | 104997561 | A | 10/2015 |
| DE | 102014219666 | A1 | 3/2016 |
| EP | 1362550 | A1 * | 11/2003 ....... G01R 33/56375 |

OTHER PUBLICATIONS

Office Action for Chinese Patent Application No. 201710518155.8 dated Mar. 2, 2020 and English translation thereof.

Office Action for Chinese Patent Application No. 201710518155.8 dated Nov. 3, 2020 and English translation thereof.

Office Action for Chinese Patent Application No. 201710513155.8 dated Mar. 3, 2021 and English translation thereof.

* cited by examiner

FIG 4

METHOD FOR POSITIONING A POSITIONABLE TABLE

PRIORITY STATEMENT

The present application hereby claims priority under 35 U.S.C. § 119 to German patent application number DE 102016211720.3 filed Jun. 29, 2016, the entire contents of which are hereby incorporated herein by reference.

FIELD

At least one embodiment of the present invention generally relates to a method for positioning a positionable table for a patient inside a medical imaging device and a medical imaging device with a positionable table for positioning a patient.

BACKGROUND

The positioning of a patient in a medical imaging device today takes place in two partial steps, namely firstly, the approximate preliminary positioning of the patient, in which the table is driven into the ring tunnel (gantry) of the imaging device and secondly, a final, more precise positioning in which a height and a longitudinal table position are manually compared again precisely using a laser cross.

Approximate preliminary positioning takes place by way of a foot switch which raises the patient to a fixed height through actuation and then moves the table into the ring tunnel until the foot switch is released. This approximate preliminary position is referred to as "patient load". The approximate preliminary positioning can, when this is performed by way of a foot switch, be performed in passing. Approximate preliminary positioning does not require much of the operator's attention, enabling further hand movements to be performed simultaneously on the patient such as, for example, the fastening of belts or cables or a conversation with the patient about the examination procedure.

For approximate preliminary positioning of the height, a uniform standard method results in the height often having to be manually readjusted. In the case of less experienced operators, as a rule, longitudinal and height positions are manually adjusted. Organ-specific default settings can be selected on the imaging device to improve approximate preliminary positioning. Depending on which organ characteristics such as, for example, head, liver or legs, are stored in a previously selected examination report, another default setting for the table height and longitudinal position to be positioned is linked to the approximate preliminary positioning. This value can be freely configured by an operator.

Subsequent more precise positioning takes place thereafter via manual control of the desired table position by way of further buttons on the imaging device. In addition to manual actuation of control buttons, more precise positioning also requires visual comparison with the position of the laser cross, which requires most of the operator's attention. To simplify fine positioning, 3-D camera systems which automatically identify the desired target position are currently used. However, these 3-D camera systems result in considerable installation work.

SUMMARY

At least one embodiment of the present invention accelerates and simplifies the positioning of a patient in a medical imaging device.

Advantageous embodiments are the subject matter of claims, the description and the figures.

According to a first embodiment, a method is disclosed for positioning a positionable table for a patient inside a medical imaging device, including:
  determining a table position as a function of an organ or body part of the patient for examination;
  ascertaining correction data for correction of the determined table position;
  determining a corrected table position based on the ascertained correction data; and
  positioning the table at the corrected table position.

According to an embodiment, a medical imaging device is disclosed with a positionable table for positioning a patient, including a determining device for determining a table position as a function of an organ or body part of the patient for examination; an ascertainment device for ascertaining correction data for correction of the predetermined table position; a correction device for correcting the determined table position based on the ascertained correction data; and a positioning device for positioning the table in the corrected table position.

According to an embodiment, a medical imaging device is disclosed with a positionable table for positioning a patient, including:
  a memory storing computer-readable instructions; and
  one or more processors configured to execute the computer-readable instructions such that the one or more processors are configured to
    determine a table position as a function of an organ or body part of the patient for examination;
    ascertain correction data for correction of the table position;
    determine a corrected table position based on the ascertained correction data; and
    a positioning device to position the table based upon the corrected table position.

BRIEF DESCRIPTION OF THE DRAWINGS

Example embodiments of the invention are shown in the diagrams and are described in more detail hereinafter.
The diagrams show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment, a method is disclosed for positioning a positionable table for a patient inside a medical imaging device, including:

determining a predetermined table position as a function of an organ or body part of the patient for examination; of ascertaining correction data for correcting the predetermined table position;

correcting the predetermined table position based on the ascertained correction data; and positioning the table in the corrected table position.

The method of at least one embodiment results in the technical advantage, for example, of enabling a manual readjustment of the table position to be omitted.

In an advantageous embodiment of the method, the table position comprises a vertical table position and/or a longitudinal table position. This results, for example, in the technical advantage of enabling different directions of the table position to be corrected.

In a further advantageous embodiment of the method, the correction data is ascertained on the basis of patient data of the patient for examination. This results, for example, in the technical advantage of enabling the table position to be adjusted patient-specifically.

In a further advantageous embodiment of the method, the patient data comprises a gender, a date of birth, a weight, a position, a height, a body mass index, an ethnicity and/or an age of the patient. This results, for example, in the technical advantage of particularly suitable parameters being used for the adjustment of the table position.

In a further advantageous embodiment of the method, the weight of the patient is automatically determined by a weighing appliance. This results, for example, in the technical advantage of enabling omission of the manual entry of the weight as patient data and the degree of accuracy being increased.

In a further advantageous embodiment of the method, the position and/or height of the patient is automatically determined by a camera. This results, for example, in the technical advantage of enabling omission of the manual entry of the height and the position as patient data and the degree of automation being increased.

In a further advantageous embodiment of the method, the correction data is ascertained on the basis of previous manual positioning of the table in conjunction with the corresponding patient data of the patient for examination. This results, for example, in the technical advantage of the method being self-learning.

In a further advantageous embodiment of the method, the correction data is obtained on the basis of an interpolation between existing data points. This results, for example, in the technical advantage of the accuracy of a positioning being improved.

In a further advantageous embodiment of the method, the correction data is obtained on the basis of an adjustment theory between existing data points. This results, for example, in the technical advantage of the accuracy of the positioning being improved.

According to an embodiment, a medical imaging device is disclosed with a positionable table for positioning a patient, including a determining device for determining a table position as a function of an organ or body part of the patient for examination; an ascertainment device for ascertaining correction data for correction of the predetermined table position; a correction device for correcting the determined table position based on the ascertained correction data; and a positioning device for positioning the table in the corrected table position.

By this, the same technical advantages are achieved as by the method according to the first embodiment.

In an advantageous embodiment of the imaging medical device, the ascertainment device is designed to ascertain correction data based on patient data of the patient for examination. This likewise results, for example, in the technical advantage of enabling the table position to be adjusted patient-specifically.

In a further advantageous embodiment of the medical imaging device, the patient data comprises a gender, a date of birth, a weight, a position, a height, a body mass index, an ethnicity and/or an age of the patient. This likewise results, for example, in the technical advantage of particularly suitable parameters being used for adjustment of the table position.

In a further advantageous embodiment of the imaging medical device, the medical imaging device comprises a weighing appliance for the automatic determination of the weight of the patient. This likewise results, for example, in the technical advantage of enabling omission of the manual entry of the weight as patient data and the degree of automation being increased.

In a further advantageous embodiment of the medical imaging device, the medical imaging device comprises a camera for the automatic determination of the position and/or height of the patient. This likewise results, for example, in the technical advantage of enabling omission of the manual entry of the height and the position as patient data and the degree of automation being increased.

In a further advantageous embodiment of the imaging medical device, the ascertainment device is designed to ascertain correction data based on previous manual positionings of the table in conjunction with the corresponding patient data of the patient for examination. This likewise results, for example, in the technical advantage of the medical imaging device being self-learning.

Figure 1:
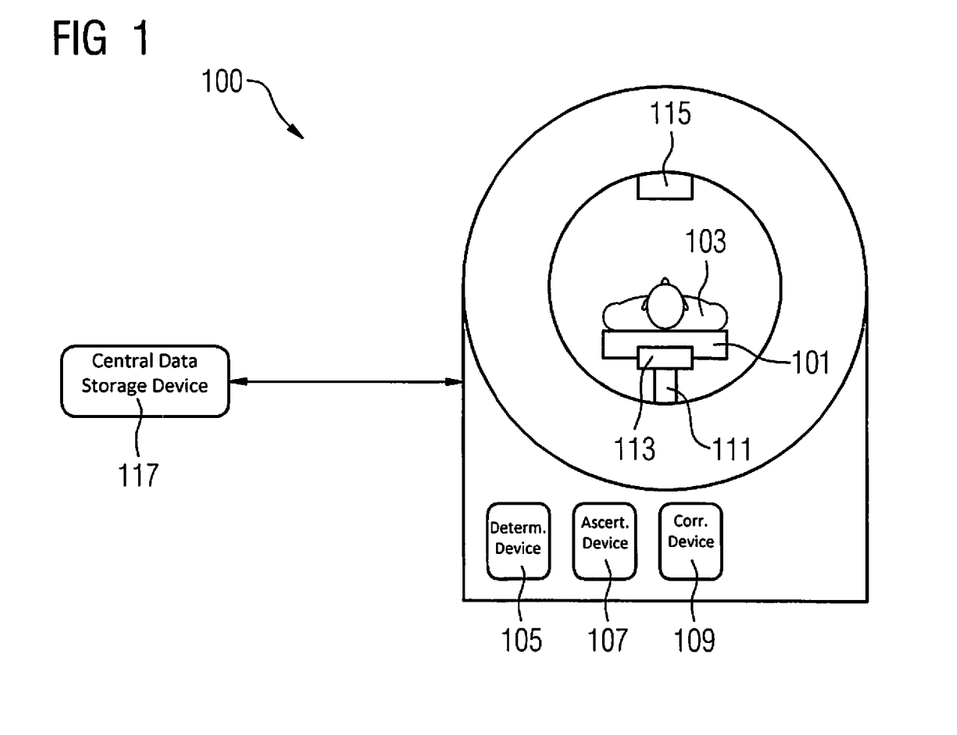
FIG. 1 A diagrammatic representation of an imaging device.

FIG. 1 shows a diagrammatic representation of a medical imaging device 100. A subtask when performing an imaging examination of a patient 103 in the medical imaging device 100 includes positioning the patient 103 in a suitable initial position for the topogram. The imaging device 100 is, for example, a computer tomography scanner (CT), a positron emissions tomography scanner (PET-CT), a magnet resonance tomography scanner (MRT) or a single-photon emission computer tomography scanner and computer tomography scanner (SPECT-CT).

For this purpose, a medical imaging device 100 comprises a positionable table 101 for positioning a patient 103 for the medical imaging examination which brings the patient 103 into the isocenter for examination. Positioning can take place in a vertical direction by altering the table height and positioning can take place in a horizontal direction by altering the longitudinal table position. For this purpose, the imaging device 100 comprises a positioning device 111 for positioning of the table 101 in a predetermined table position which, for example, is constituted by way of controllable, electric servo motors.

A determining device 105 is used for determining a first predetermined table position as a function of an organ or body part of the patient for examination 103. The determining device(s) 105 are, for example, constituted by a processor with a digital memory which ascertains the predetermined table position by entering an organ or body part of the patient for examination 103 based on a look-up table. In this way, data is obtained for a first approximate positioning of the table 101.

In addition, an ascertainment device 107 for ascertaining correction data is used for correction of the predetermined table position. In this way, data is obtained for a more precise positioning of the table 101. The ascertainment device 107 is, for example, likewise constituted by a processor with a digital memory which calculates correction data for more precise positioning based on further patient data of the patient for examination 103.

A correction device 109 is used for the fine correction of the first approximate table position based on the ascertained correction data, for example, through the addition of correction data to the initially defined table position. The ascertainment device 107 is, for example, likewise constituted by a processor with a digital memory which can perform the corresponding calculations. The ascertainment device 107 is, for example, designed to ascertain the correction data based on patient data of the patient for examination 103 such as a gender, a date of birth, a weight, a position, a height, a body mass index, an ethnicity and/or an age of the patient 103. The ascertainment device 107 is designed to ascertain the correction data based on previous manual positionings of the table 101 in conjunction with the corresponding patient data of the patient for examination 103.

In addition, the medical imaging device 100 comprises a weighing appliance 113 for the automatic determination of the weight of the patient 103 as patient data or a camera 115 for the automatic determination of the height or position of the patient 103 as patient data.

The entire positioning of the patient 103 can be performed completely by the medical imaging device 100 with the aid of the actuation of a single button, without the need to use a 3-D camera. The realization of the user interaction of the positioning function is independent of this. The positioning function can, for example, be realized by way of a foot switch, a control box, a remote control, gantry buttons, soft keys on a software user interface, gesture control or voice control.

The medical imaging device 100 can be connected to a central data storage device 117 by way of a data line with which a plurality of further imaging devices 100 is connected.

Figure 2:
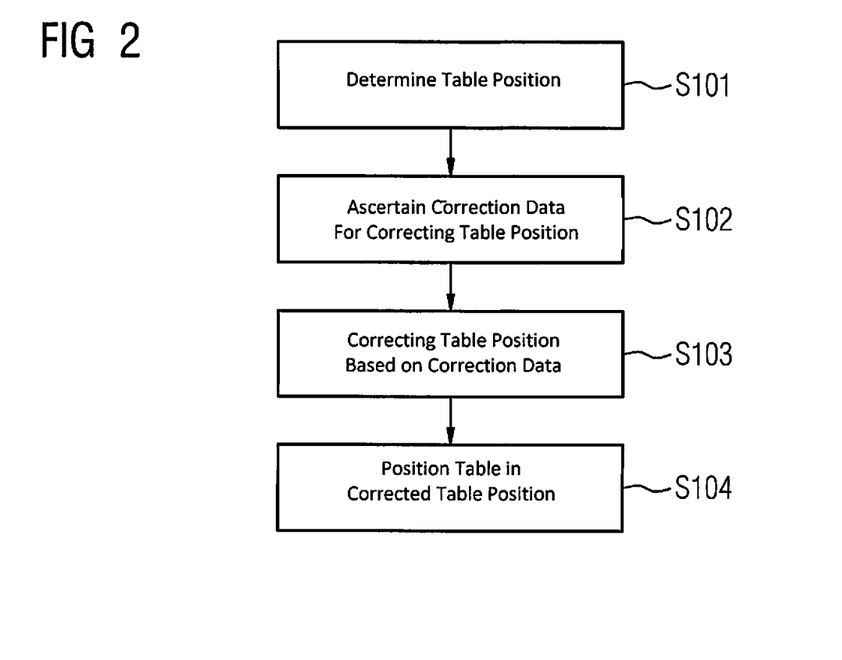
FIG. 2 A block diagram of a method.

FIG. 2 shows a simplified block diagram of a method for positioning the positionable table 101 for the patient 103 inside the medical, imaging device 100. The method comprises the step S101 of determining the predetermined table position as a function of an organ or body part of the patient for examination 103; the step S102 of ascertaining the correction data for correcting the predetermined table position; the step S103 of a correction S103 of the predetermined table position based on the ascertained correction data; and the step S104 of positioning the table 101 in the corrected table position.

Figure 3:
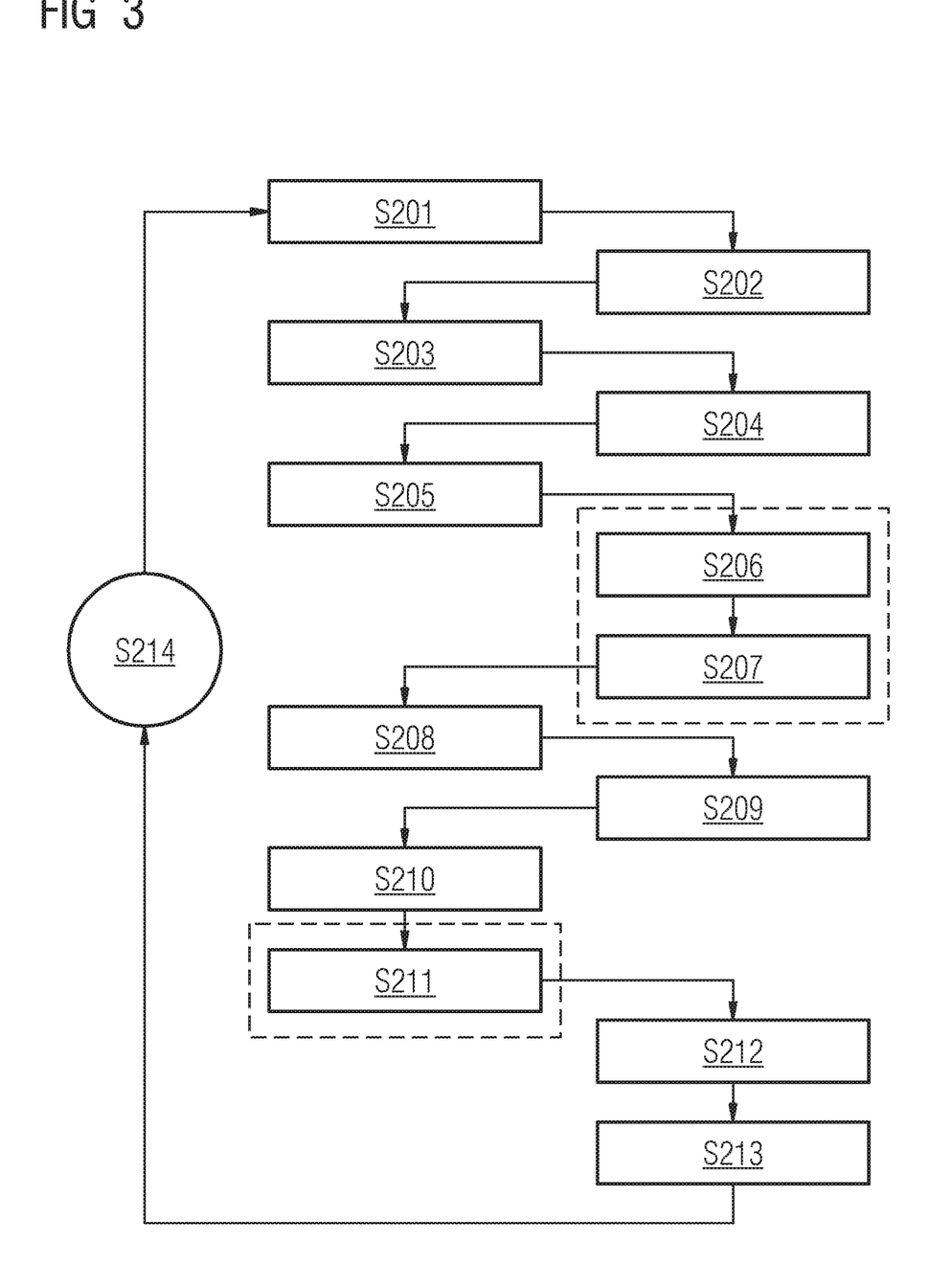
FIG. 3 A further block diagram of a method, and
  FIG. 4 A further block diagram of the method.

FIG. 3 shows a more comprehensive block diagram of the method for positioning the positionable table 101. In a step S201, the patient 103 is first recorded with workflow standardization before positioning so that the digital patient record includes the type of examination to be performed.

In step S202, patient data is provided by way of the digital patient record such as, for example, age, gender or clinical indication. In step S203, an examination report based on the clinical indication of the patient record is selected.

In step S204, a predetermined, approximate table position is corrected based on the patient data which was entered in a previously trained model. In step S205 the patient 103 is positioned on the table 101.

In step S206, the weight and the height of the patient 103 are automatically determined if the imaging device 100 includes corresponding sensors. Subsequently, in step S207, the first predetermined table position is corrected on the basis of the available sensor data.

In step S208, the button for retracting the patient 103 into the medical imaging device 100 is activated. In step S209, the table 101 is automatically driven to the corrected table position. As soon as the table 101 has reached the corrected table position, in step S210 the button for retracting the patient 103 is released.

In step S211, a manual readjustment of the position of the table 101 can be undertaken by the operator. If the medical imaging device 100 has already been trained previously, this step can be omitted.

In step S212, the manually adjusted table position is stored together with the patient data and the sensor data. In step S213, an algorithmic model based on the additional data set with the patient data and the manual adjustment of the table 101 is trained by the operator. In step S214, the method is continued with a new patient 103.

Figure 4:
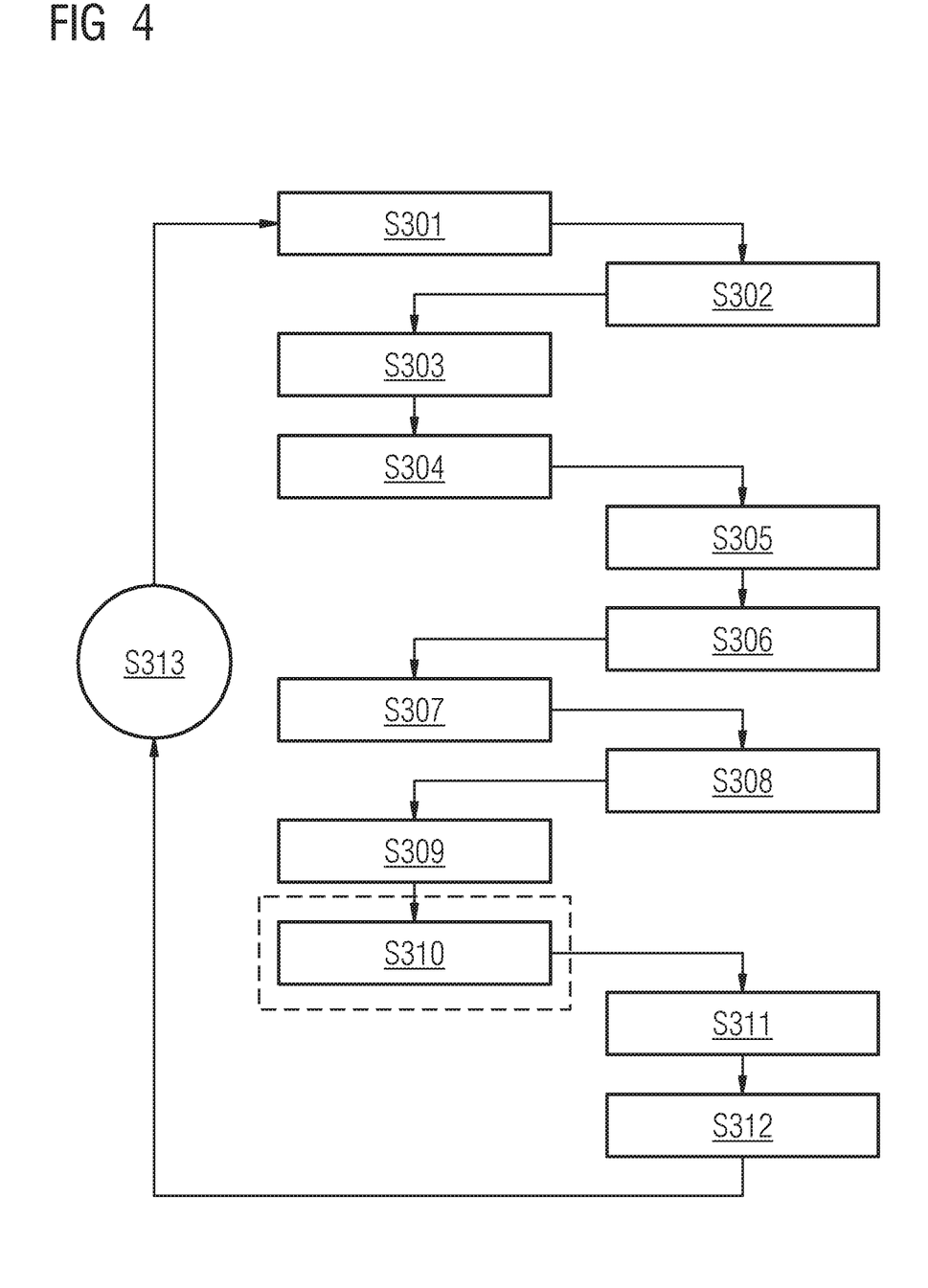

FIG. 4 shows a further more comprehensive block diagram of the method for positioning the positionable table 101. In a step S301, the patient 103 is first registered with workflow standardization before positioning so that the digital patient record includes the kind of examination to be performed.

In step S302, patient data relating to the digital patient record such as, for example, age, gender or clinical indication is provided. In step S303, an examination report based on the clinical indication of the patient record is selected.

In step S304, the patient 103 is positioned on the table 101. In step S305, a 3-D camera determines a three-dimensional model with three-dimensional data of the patient 103 and an ideal isocenter and a table position for the examination are determined.

In step S306, an algorithm previously trained on the basis of a plurality of manual adjustments corrects the initially defined table position according to an operator adjustment, the patient data and the three-dimensional data.

In step S307, the button for retracting the patient 103 into the medical imaging device 100 is activated. In step S308, the table 101 is automatically driven to the corrected table position. As soon as the table 101 has reached the corrected table position, in step S309 the button for retracting the patient 103 is released.

In step S310, a manual readjustment of the position of the table 101 is undertaken by the operator. If the medical imaging device 100 corresponds to the adjusted position of the assessment of the operator, this step may be omitted.

In step S311, the manually adjusted table position is stored together with the patient data and the sensor data. In step S312, an algorithmic model based on the additional data set with the patient data and the manual adjustment of the table 101 is trained by the operator. In step S313 the method is continued with a new patient 103.

Generally speaking, the positioning of the patient 103 in the imaging device 100 can be achieved by way of the following steps:

(1) In the medical imaging device 100, the aforementioned organ-specific adjustment options are available for the table position, i.e. table height and longitudinal position. In principle, the manual fine positioning of the table position can in principle also be performed by an operator after the automatic execution of positioning.

(2) For automatic positioning, a correction of the organ-specific default setting is undertaken on the basis of patient data. As soon as a patient 103 has been recorded, individual patient data can be obtained such as, for example, gender, date of birth, weight, position, height, body mass index, ethnicity or age.

From this patient data, the correct table position can be estimated in advance, taking into account a demographic distribution. This can, for example, be realized by first specifying both a value for a minimum height and a value for a maximum height for each organ-specific default setting. Interpolation as a function of the available patient data then takes place between these two values.

In another embodiment, there may simply be an offset between the height for a female and a male thorax examination. This results in a gender-specific adjustment for the table position to be approached, in which a default value for the thorax examination is altered for the table position to be approached by the offset value depending on the gender of the patient 103.

(3) For automatic positioning, a self-learning adjustment of the table position to a typical patient population of the imaging medical device 100 can be performed. Regardless of whether organ-specific adjustment options (1) or their demographic correction (2) are used, the positioning depends on which patient population is being examined by the medical imaging device 100. For example, a patient population in the USA has different properties to a patient population in Japan. Therefore, the table position to be approached can be adjusted by way of self-learning algorithms in the course of a series of use.

The algorithms are trained with each manual correction performed by the operator after automatic positioning of the table position.

For the step (1), this can take place by adjusting the organ-specific table position for each automatic positioning to the average value of previous table positions which have been used for these organ characteristics or the selected examination report.

In the event (2), self-learning can be realized, for example, by determining, i.e. fitting the selected interpolation function between the two default values at all table positions previously adjusted for an organ characteristic by way of an adjustment theory.

(4) For automatic positioning, cross validation methods and genetic algorithms can be applied to the method described in (3). In the event of demography-dependent default settings (2), self-learning algorithms can employ data mining to autonomously adjust the interpolation function to the table positions previously adjusted on the imaging device 100. For example, it is possible to establish whether the dependence of the table position is better determined by a polynomial of the n-th degree or by a logarithmic dependence for a lung report.

Such a parameter range which, for example, is adjusted to 100 to 1000 input measured values, no longer needs to be trained by a fit function to predict the next patient 103 as the prediction quality may suffer as a result.

Better results can be achieved with the aid of cross validation methods in which the possible interpolation functions are assessed with regard to their ability to predict the n-th value of the table position from n−1 table positions.

In the wide parameter range of various interpolation functions for the numerous possible demographic data, if these have been evaluated in this way, genetic algorithms can be used so that only relevant demographic data with the best respective interpolation function are combined such that meaningful modeling of the ideal table position results.

The result is a set of modeling functions which is individually adjusted to an existing patient population. Taking account of the existing demographic data, the modeling functions enable as precise a prediction as possible of the table position of the next patient 103 desired by an operator for the selected examination report or the organ characteristics specified therein.

(5) For automatic positioning, an independent survey of the anatomical patient data which are used for step (3) or (4) can take place.

For the successful modeling of the table position to be adjusted as a function of the patient data, steps (2) and (3) also use such patient data which is as a rule not available for the recording of the patient 103. The patient data may, for example, comprise a weight of the patient 103 which is determined by a weighing appliance 113 integrated in the table 101. The weight of the patient 103 can thus be ascertained independently by the imaging device 100 before positioning and included in the calculation of the default settings of the table position to be used for this patient 103.

However, the weight can also be used after the positioning concluded by the operator to train the self-learning algorithms in (2) or (3) using this information.

The patient data may, for example, comprise the height and position of the patient 103 which are captured from a camera system. For example, an image from a 2D-camera 115 is sufficient to determine the height of the patient 103 precisely enough and to improve the prediction of the table position to be adjusted as a result. The position of the patient 103 on the table 101, for example, lying on their stomach, lying on their back, head first or feet first, can be simply determined on the basis of the 2-D image data.

If the perspective of the camera image is not broad enough to fully display the patient 103, in the course of positioning the patient 103 can be pushed through under the camera 115 to thus determine the height or position. As the imaging device 100 travels over most of the body of the patient 103 as the patient 103 is retracted, the height and the position of the patient 103 can be determined in real time by detecting landmarks.

This height or position can be entered in real time as parameters in interpolation algorithms to predict the table position before conclusion of the positioning process. In this case, a positioning functionality which does not require any further manual fine positioning is achieved.

(6) For automatic positioning, operator-dependent modeling parameters for steps (1)-(5) can be used. Although in principle only a single correct isocentering of the patient 103 exists, nevertheless not all operators of the imaging medical device 100 adjust the patient positioning immediately.

Even if variations between the operators are caused by different misjudgments, acceptance by the operator can be disturbed by the imaging device 100 proposing values other than those the operator would select. In this case, the operator may reject the automatic positioning although the operator is probably making a greater mistake themselves than the automatic positioning in estimating the isocenter.

If the respective operators identify themselves on the imaging device 100, each operator can be assigned a different set of default settings or fit functions/parameters. These operator-specific default settings can continue to be fitted on all patients 103 positioned on the imaging device 100. However, those data points which the operator himself has generated by positioning the patient 103 can be reinforced for each operator by an increased weighting in the influence on the fit process or cross-validation process.

If this different weighting between the data points of individual operation is reduced compared with the data points of other operators, the operator can slowly be guided from its self-adjusted, suboptimal isocentering to an isocentering which complies with other operators.

(7) For automatic positioning, the accuracy of steps (3)-(6) can be increased by increasing the database by way of a central data storage device (cloud) with which a plurality of imaging devices 100 is connected.

Many medical facilities such as, for example, radiology practices, only examine a few patients a day. In this case, it can take a long time for a sufficient quantity of data points to be collected during positioning for each individual organ characteristic to thus enable self-learning modeling of the table position.

This problem can be solved by coupling the imaging device 100 to a central data storage device (cloud storage) 117 which gathers positioning data points of all the connected imaging devices 100. This volume of data points can then be retrieved to enable optimum modeling of the table position for each facility.

Not all the collected data points of the central data storage devices need to be evaluated for the individual modeling set of a facility. Instead, the data of individual facilities with a patient population which is sufficiently similar in terms of physiognomy can be chosen selectively. This can be achieved by only including data points for modeling originating from facilities in the local vicinity of the target facility.

Data points of facilities which despite being further away have patient populations with a similar physiognomy can fail to be taken into consideration in the process. The problem of selection can be solved by way of cross validation methods and genetic algorithms, by only selecting the data points of facilities with respective data points suitable for enabling a more precise prediction for the target facility.

This database in the central data storage device makes it possible to ensure that upon delivery i.e. without a single patient 103 having been positioned thereon, imaging devices 100 are already able to usefully model the table position.

The data from the central data storage device which is used for modeling can also be filtered to avoid unusable positioning being included in the modeling. Useful quality criteria can be, for example, the establishment of operators with a high reputation (super user), an evaluation of the image quality which has been obtained in the examination or consideration as to whether the table position had to be subsequently corrected in the course of subsequent examination.

(8) Analogous to the target table height as an adjustment of the table position, it is possible to configure a default setting for the longitudinal table position dependent on the log. The longitudinal table position can likewise be modeled for individual patients and examinations on the basis of demographic input parameters or measured patient properties.

To model the longitudinal table position, the position of the patient 103 relative to the table 101 can be determined, for example, by a camera 115. In the absence of a camera 115, markings on the table 101 can enable the patient 103 either to be positioned at the same location or depending on the organ to be examined, at different locations on the table 101. For the automatic adjustment of the longitudinal table position, the accuracy can be increased if the patient data available for modeling is automatically collected by sensors, for example, by automatically measuring weight and height (as in step (5)). The accuracy of the modeling of the automatic adjustment of the longitudinal table position can also be increased by a large database.

The steps (5), (6) and (7) can be combined using 3-D autopositioning. An algorithm can be used to automatically ascertain the table height from the height profile measured by a 3-D camera. The longitudinal table position can either be predefined by the operator or likewise ascertained from the landmarks of the height profile and approached automatically.

Depending on whether the operator agrees with the table position, this can then be accepted as it is automatically approached by the imaging device 100 or manually readjusted.

While isocentering can be automatically approached with this method, the best longitudinal table position can be determined less deterministically from 3-D measured values but also depends on the desired clinical issue. Furthermore, the longitudinal table position depends on the preference of the operator, in particular, whether the operator would like to have a somewhat larger overview image across the target organs of the patient 103 in the topogram or whether the operator chooses the most concise topogram possible to reduce radiation exposure.

In this point, the combination of 3-D autopositioning can be improved by combination with step (6), by learning from the operator preference. As described in step (5), for each positioning procedure a 3-D model of the patient 103 is created from which all the data necessary for modeling can be extracted.

The algorithm suggests a table height and a longitudinal table position which the operator corrects manually. The result is stored as the table position preferred by the operator together with the patient data which has been measured by the 3-D camera. This patient data may include measured values such as, for example, height at head, chest, stomach, length of the thorax, thigh, arm or shoulder width.

Which patient data is relevant for the modeling of the ideal table position of a particular type of examination can be determined, as in step (4), by way of genetic algorithms and cross validation methods. The more positionings are performed on the imaging device 100 by an operator, the more precisely the algorithm can learn about its modeling according to the preference of the operator. Finally, the imaging device 100 can automatically approach the optimum table position without any further intervention by the operator.

Determining the table position involves a deterministic process which can be better determined by automatism than by an experienced operator. However, the adjustment of the longitudinal table position also depends on the circumstances of the examination and operator preference. Accordingly, it may be useful to only employ step (9) for the determination of the longitudinal table position.

Generally speaking, the method enables an automatic positioning function to also be obtained without a 3-D camera, dispensing with the need for the costly installation of a 3-D camera. Nevertheless, if there is a 3-D camera available, a longitudinal table position can be more precisely trained.

In an expert mode, only that data originating from the positionings undertaken by the operator himself is primarily used to train the algorithms. It is thereby assumed that the operator obtains precise positioning and the imaging device 100 learns from the operator. Measured values from other operators are either not taken into consideration or given a lower weighting.

The value for the expert operator lies in the imaging device 100 knowing after a certain number of positioning moves, i.e. as soon as the algorithm has sufficient measured values at its disposal to model the target position for individual patients and logs with sufficient accuracy, the preferred adjustments of the expert operator and predetermining these during positioning. This dispenses with the need for manual fine positioning. There are time savings during patient examination and the operator can devote himself to the care of the patient 103 during automatic positioning of the table 101.

In an initial mode, measured values not primarily originating from the operator are used to train the algorithm. In this case, the medical imaging device 100 is already delivered with a complete, cloud-based modeling set. An inexperienced operator can therefore rule out incorrect positioning without a cumbersome learning process. In this case, it suffices for the operator to select an examination report with a correct organ characteristic. Based on the knowledge of all the previous operators, the imaging device 100 selects suitable patient and protocol-specific positioning. In the initial mode, there are also time savings during patient examination and the operator can devote himself to the care of the patient 103 during the automatic positioning of the table 101.

A further advantage for manufacturers of medical imaging devices 100 is that the cloud-based method can be used to enable new imaging devices 100 with modeling parameters which include the entire knowledge of all the previous operators to also be delivered.

All the features explained and shown in connection with individual embodiments of the invention can be provided in different combinations in the object according to the invention to simultaneously realize their advantageous effects.

All the steps of the method can be implemented by devices which are suitable for the execution of the respective step. All the functions which are executed by objective features, can be a step of a method.

The scope of protection of the present invention is specified by the claims and is not restricted by the features explained in the description or shown in the figures.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for positioning a positionable table for a patient inside a medical imaging device, the method comprising:
   determining, via a processor of the medical imaging device, a first approximate table position as a function of an organ or body part of the patient for examination;
   ascertaining, via a processor of the medical imaging device, correction data from a database of a plurality patient models for correction of the determined first approximate table position to a second more precise table position relative to the first approximate table position by importing patient data for correction of the first table position;

determining, via a processor of the medical imaging device, a corrected table position based on the imported patient data and a self-learning algorithm; and positioning, via a processor of the medical imaging device, the table at the corrected table position before initiating a medical imaging procedure via the medical imaging device, wherein the patient data includes at least one of a gender, clinical indication, and an age of the patient included in an examination report prepared prior to positioning the table, wherein the self-learning algorithm is trained by storing, in a memory, imported patient data of a plurality of patients and manual corrections of table positions that follows automatic positionings of table positions.

2. The method of claim 1, wherein the table position comprises at least one of a vertical table position and a longitudinal table position.

3. The method of claim 1, wherein the weight of the patient is automatically determined by a weighing appliance of the medical imaging device.

4. The method of claim 1, wherein at least one of a position and a height of the patient is automatically determined by a camera.

5. The method of claim 1, wherein the correction data is ascertained based on previous manual corrections of the table in conjunction with corresponding patient data of the patient for examination.

6. The method of claim 1, wherein the correction data is ascertained based on an interpolation between existing data points.

7. The method of claim 1, wherein the correction data is ascertained based on an adjustment theory between existing data points.

8. A medical imaging device including a positionable table for positioning a patient, comprising:

a memory storing computer-readable instructions; and
one or more processors configured to execute the computer-readable instructions such that the one or more processors are configured to determine a first table position as a function of an organ or body part of the patient for examination based on a look-up table stored in the memory;

ascertain correction data for correcting the first table position to a more precise second table position relative to the first table position by importing patient data for correction of the first table position;

determine a corrected table position based on the imported patient data and a self-learning algorithm; and at least one motor for positioning the table at the corrected table position based on an output of the self-learning algorithm, wherein the patient data includes at least one of a gender, clinical indication, and an age of the patient, wherein the self-learning algorithm is trained by storing, in a memory, imported patient data of a plurality of patients and manual corrections of table positions that follows automatic positionings of table positions.

9. The medical imaging device of claim 8, wherein the one or more processors are configured to ascertain the correction data based on patient data of the patient for examination.

10. The medical imaging device of claim 9, wherein the patient data comprises at least one of a date of birth, a weight, a height, a body mass index, and an ethnicity of the patient.

11. The medical imaging device of claim 10, further comprising:

a weighing appliance for automatic determination of the weight of the patient.

12. The medical imaging device of claim 10, further comprising:

a camera for automatic determination of at least one of a position and height of the patient.

13. The medical imaging device of claim 10, wherein the one or more processors configured to ascertain the correction data based on previous manual positionings of the table in conjunction with corresponding patient data of the patient for examination.

14. A medical imaging device including a positionable table for positioning a patient, comprising:

a memory storing computer-readable instructions; and
one or more processors configured to execute the computer-readable instructions such that the one or more processors are configured to determine a first approximate table position as a function of an organ or body part of the patient for examination;

ascertain correction data for correction of the first approximate table position to a second more precise table position relative to the first approximate table position by importing patient data for correction of the first table position;

determine a corrected table position based on the imported patient data and a self-learning algorithm; and at least one motor to position the table based upon the corrected table position before initiating a medical imaging procedure via the medical imaging device, wherein the patient data includes at least one of a gender, clinical indication, and an age of the patient, wherein the self-learning algorithm is trained by storing, in a memory, imported patient data of a plurality of patients and manual corrections of table positions that follows automatic positionings of table positions.

15. The method of claim 3, wherein at least one of a position and height of the patient is automatically determined by a camera.

16. The medical imaging device of claim 14, wherein the correction data is ascertained based on previous manual positionings of the table in conjunction with corresponding patient data of the patient for examination.

17. The method of claim 1, wherein the patient data includes a date of birth of the patient.

18. The method of claim 1, wherein the patient data includes a weight of the patient.

19. The method of claim 1, wherein the patient data includes a height of the patient.

20. The method of claim 1, wherein the patient data includes a body mass index of the patient.

21. The method of claim 1, wherein the patient data includes an ethnicity of the patient.

* * * * *